United States Patent [19]

Stevens et al.

[11] Patent Number: 4,837,161
[45] Date of Patent: Jun. 6, 1989

[54] METHOD FOR REAGENT ADDITION TO A FLOWING LIQUID CARRIER STREAM

[75] Inventors: Timothy S. Stevens; Nile N. Frawley; Daniel J. Swart, all of Midland, Mich.; William C. Harris, Neshanic Station, N.J.; Deborah E. Diedering, Sanford, Mich.; Lawrence W. Nicholson; L. David Rothman, both of Midland, Mich.

[73] Assignee: The Dow Chemical Company, Midland, Mich.

[21] Appl. No.: 900,038

[22] Filed: Aug. 25, 1986

Related U.S. Application Data

[63] Continuation-in-part of Ser. No. 725,861, Apr. 22, 1985, abandoned, and a continuation-in-part of Ser. No. 709,141, Mar. 7, 1985, abandoned, and a continuation-in-part of Ser. No. 707,772, Mar. 4, 1985, abandoned, said Ser. No. 707,772, is a continuation of Ser. No. 15,830, Feb. 18, 1987, abandoned.

[51] Int. Cl.$^4$ .................... G01N 30/06; G01N 35/08
[52] U.S. Cl. .................... 436/52; 210/198.2; 210/321.6; 210/321.82; 210/321.84; 210/637; 210/649; 210/656; 422/70; 422/81; 422/82; 436/53; 436/161; 436/178
[58] Field of Search .................... 422/70, 68, 69, 81, 422/82; 436/161, 178, 174, 52, 53; 210/198.2, 656, 637, 659, 649, 321.1, 321.6, 321.82, 321.84; 73/61.1 C

[56] References Cited

U.S. PATENT DOCUMENTS

| | | | |
|---|---|---|---|
| 3,495,943 | 2/1970 | Kapff | 23/230 |
| 3,850,203 | 11/1974 | Shobert | 138/103 X |
| 3,891,556 | 6/1975 | Richardson et al. | 210/490 X |
| 4,022,249 | 5/1977 | de Putter | 210/342 X |
| 4,158,629 | 6/1979 | Sawyer | 210/321.1 X |
| 4,239,624 | 12/1980 | van Zon | 210/321.1 X |
| 4,251,218 | 2/1981 | Diggens | 23/230 |
| 4,378,981 | 4/1983 | Otstot et al. | 210/321.1 X |
| 4,448,691 | 5/1984 | Davis | 210/656 |
| 4,451,374 | 5/1984 | Peterson et al. | 210/656 |
| 4,549,965 | 10/1985 | Davis | 210/635 |
| 4,597,873 | 7/1986 | Almaula | 210/649 |

FOREIGN PATENT DOCUMENTS 8200773 3/1982 PCT Int'l Appl. .

OTHER PUBLICATIONS

Nau et al, Anal. Chem., vol. 51, No. 3, pp. 424–428, 1979.

Primary Examiner—Robert J. Hill, Jr.
Attorney, Agent, or Firm—Timothy S. Stevens

[57] ABSTRACT

An analytical chemistry apparatus and method for introducing a reagent into a flowing stream of liquid carrier in order to quantitatively analyze one or more components of a sample added into the carrier. The reagent is permeated across a short section of membrane having relatively large pores. The use of such a membrane: (a) allows the membrane to be protected from physical damage by covering it with a perforate structure; (b) significantly reduces bandspreading across the membrane reagent addition device; (c) reduces the pressure drop across the membrane reagent addition device; and (d) still allows for the permeation of an effective amount of the reagent into the carrier. The reagent is preferably pressurized to minimize leakage of carrier across the membrane and the reagent can be self-pressurized by essentially completely filling the reagent reservoir of the invention with reagent and then hermetically sealing the reservoir.

8 Claims, 7 Drawing Sheets

METHOD FOR REAGENT ADDITION TO A FLOWING LIQUID CARRIER STREAM

CROSS-REFERENCE TO RELATED APPLICATION

This application is a continuation-in-part of copending application Ser. No. 725,861, filed Apr. 22, 1985, now abandoned, application Ser. No. 709,141, filed Mar. 7, 1985 and application Ser. No. 707,772, filed Mar. 4, 1985, now abandoned which are hereby incorporated by reference. Application Ser. No. 707,772, filed Mar. 4, 1985, now abandoned, was continued as application Ser. No. 015,830, filed Feb. 18, 1987, now abandoned.

FIELD OF THE INVENTION

The invention relates to an improved method and apparatus by which a reagent can be added to a flowing stream of a liquid carrier in the field of liquid chromatography to enhance the sensitivity of detection and similarly to a flowing stream of a liquid carrier in the field of Flow Injection Analysis (FIA).

BACKGROUND OF THE INVENTION

Membrane reagent addition devices have been used to improve detection in modern high performance liquid chromatography (HPLC). One example of a membrane reagent addition device is disclosed in U.S. Pat. No. 4,448,691 to The membrane reagent addition device taught by that patent utilized relatively long lengths of tubular form membranes of a relatively small pore size or relatively long lengths of nonporous tubular membranes, suspended in a space containing a reagent for permeation transfer of an effective amount of the reagent through the membrane and into the liquid chromatographic carrier or flow injection analysis carrier.

Several problems are associated with the prior membrane reagent addition devices. The relatively long tubular membranes are subject to being damaged during device construction by becoming pinched in the seams of the device and during operation can become tangled in a stirrer used to stir the reagent. In addition, the relatively long tubular membranes cause deleterious bandspreading which can reduce the resolution of closely eluting peaks in chromatographic applications and can reduce the sampling frequency in FIA applications.

The present invention solves these problems by using a short length of relatively large pore size tubular membrane (or a limited area of sheet form membrane if equivalently utilized). The relatively short length of membrane reduces bandspreading significantly to as low as 50 µl or less. In addition, a short length of membrane is less likely to become pinched in the seams of a membrane reagent addition device during device construction and can be protected from damage from a stirring bar by covering the membrane with a high strength perforate structure.

The prior art did not suggest the use of relatively large pore size membranes or the use of short lengths of tubular membranes. The relatively long lengths of tubular membranes used in the prior art were needed to permeate enough reagent into the analytical stream to be effective. Large pore size membranes were probably not used in the prior art due to the problem of excessive leakage across the membrane as discussed in detail below.

A characteristic of membrane reagent addition devices is the tendency for pressure to be higher on the carrier side of the membrane than on the reagent side. This pressure differential is caused by the structural features of the known devices and often exacerbated by the often used reaction coil or packed bed in fluid communication with the reagent addition device and the detector. The reaction coil or in the alternative, the packed bed, serves to homogenize the constituents of the carrier and in some cases, increase the time necessary to complete a reaction between the carrier components. In addition, the relatively long length of tubular membrane as used in prior membrane reagent addition devices, has an associated carrier pressure drop along the inside (bore) of the tubular membrane. Therefore, pressurizing the reagent on the outside of a relatively long tubular membrane is not an effective solution to minimize excessive leakage of carrier across the membrane into the reagent when the membrane has relatively large pores. If the reagent is pressurized to a pressure equal to the carrier pressure in the end portion of such a tubular membrane, then excessive carrier leakage across the membrane can occur at the beginning portion of the tubular membrane. If the reagent is pressurized to a pressure equal to the carrier pressure in the beginning portion of such a tubular membrane, then excessive amounts of reagent can pass across the membrane at the end portions of the tubular membrane. If the reagent is pressurized to a pressure equal to the carrier pressure in the middle portion of such a tubular membrane, then excessive amounts of carrier can still pass across the membrane at the beginning portion of the tubular membrane and excessive amounts of reagent can pass across the membrane at the end portions of the tubular membranes.

Relatively large pore size membranes are desirable in membrane reagent addition devices despite these problems. In the prior membrane reagent addition devices the membrane often had to be selected for a specific reagent. Each reagent/membrane combination needed to be tested to ensure that enough reagent would permeate the membrane to be effective. The use of a relatively large pore size membrane offered the promise of an unlimited ability to permeate almost any reagent but the problems described in the previous paragraph are believed to have frustrated their use.

The present invention solves the aforementioned problem of excessive leakage across a relatively large pore size membrane by using a short length of such a tubular membrane which significantly reduces the pressure drop of carrier along the inside of the tubular membrane. Surprisingly, the short length of such a tubular membrane (or limited area of sheet form membrane if equivalently utilized) still permeates an effective amount of reagent into the carrier stream. In many applications it is still necessary to pressurize the reagent chamber with, for example, compressed air to prevent excessive carrier leakage across the membrane and pressurizing the reagent space of a membrane reagent addition device employing a short length of tubular membrane of relatively large pore size can overcome the aforementioned leakage problems. The present invention also comprises a novel means of pressurizing the reagent space of a porous membrane reagent addition device. This means is simply to hermetically seal the reagent space which has been essentially completely filled with reagent. In this event the pressure on each side of the porous membrane naturally and automatically equilibrates. Thus, whatever the carrier pressure is on the carrier side of the membrane (as a result of detector back pressure or back pressure through a mixing coil or mixing column) the reagent pressure automatically adjusts to approximately the same pressure as the carrier. Therefore, even when this embodiment of the invention is used to add reagent to a liquid chromatographic eluent stream before the eluent stream passes through the chromatographic column (and where the eluent pressure could be 2,000 psi, for example) the reagent will automatically self-pressurize and then effectively add reagent to the eluent stream.

Terms

The term "carrier" comprises a liquid eluent when employed with a chromatographic column and includes the effluent from said chromatographic column. The term "carrier" also comprises a liquid carrier when employed with the analytical chemical technique known as Flow Injection Analysis.

The term "excessive leakage of carrier across the membrane" means a condition wherein more than 10 percent of the carrier flow inputted to the membrane reagent addition device of the invention passes across the membrane into the reagent. The term also means a condition wherein reagent permeation across the membrane into the carrier is effectively prevented by the opposing flow of carrier across the membrane (an example of this condition is given in Example 9, below).

The term "excessive permeation of the reagent into the carrier" means a condition wherein the volume flow rate of reagent permeation across the membrane into the carrier is more than 10 percent of the volume flow rate of the carrier inputted to the membrane reagent addition device of the invention.

The term "reagent" means a chemical species or combination of species, generally dissolved in a liquid, essentially the purpose of which when permeated through the membrane into the carrier is to react chemically, directly or indirectly, with a sample component of interest or an interfering species less than perfectly resolved with respect to the sample component of interest, to produce measurable enhancement in the detection of the component of interest, or a monitored proportional derivative thereof, compared to the absence of the membrane/reagent combination. For example, a monitored proportional derivative can be produced using as a reagent the well-known derivative agent ortho-phthaldehyde (o-PA) which reacts with primary amines in the presence of thiol compounds to produce a fluorescent derivative of the amine.

In addition, the term "reagent" means a chemical species or combination of species, generally dissolved in a liquid, essentially the purpose of which when permeated through the membrane is to condition a carrier for enhanced detection of a sample component of interest. The phrase "condition a carrier" refers to a method for changing the carrier, such as chaning carrier pH, or adding a solvent to carrier which increases the kinetics of a derivatization reaction; e.g., the addition of acetone for the determination of peroxides iodometrically when the carrier is hexane.

The term "membrane" refers to a porous reagent permeable membrane having the capability of partitioning a carrier stream from the reagent, and the property to transport reagent in permeation contact with one wall surface of the membrane while rejecting from transport, at least a detectable amount of the sample component of interest, or a derivative proportional thereto. It is preferred that the membrane be a tubular form membrane, with an internal diameter within the range of from 20 to 2,000 microns, and most preferably from 200 to 1,000 microns. However, the membrane can also be in the form of a sheet.

The term "membrane" also refers to a membrane with a volume average pore diameter within the range of from greater than 125 Å to about 5,000 Å, and preferably from about 150 Å to about 2,000 Å, most preferably from about 200 Å to about 1,000 Å and with structural characteristics that do not promote severe leakage and cause the method of the invention to become inoperative. The term "average pore diameter" (Dp) is a term well-known in the art and relates to the statistical distribution of pore diameters within the membrane. The method employed herein for determining "average pore diameter" is the known technique of mercury porousimetry as described in "Advanced Experimental Techniques in Powder Metallurgy," Vol. 5, Plenum Press (1970). The term also refers to a membrane which preferably has an area, in effective contact with the reagent, of less than 150 mm$^2$, and more preferably from 1.0 mm$^2$ to 75 mm$^2$, and most preferably from 1.5 mm$^2$ to 50 mm$^2$.

The term "membrane" yet further refers to one or more tubular form membranes or one or more sheet form membranes used to partition the carrier from the reagent in the invention.

SUMMARY OF THE INVENTION

The present invention is an analytical chemistry apparatus for effectively adding reagent to a flowing stream of liquid carrier in order to quantitatively analyze one or more components of a preselected volume of sample added into said carrier wherein the apparatus comprises: a means to define a channel exposed to one side of a porous membrane having an average pore diameter of from greater than 125 Å to about 5,000 Å and through which channel the carrier flows in contact with one side of the membrane; means to define a space exposed to the other side of the porous membrane, the space containing the reagent in contact with the membrane and across which membrane the reagent permeates into the carrier; and wherein the length of the portion of the channel juxtaposed to the space through the membrane is less than about 30 cm and wherein the area of the membrane in juxtaposed contact with both the channel and the space is less than 150 mm$^2$ on the side of the membrane exposed to the space.

The membrane can comprise a tubular membrane or a sheet membrane. The membrane can comprise a polyolefin such as polypropylene.

The reagent in the space can be externally pressurized with, for example, compressed air to enhance the permeation of the reagent across the membrane into the carrier. However, the reagent can also be self-pressurized by hermetically sealing the reagent space which has been essentially completely filled with reagent. In this event, carrier initially passes through the porous membrane into the reagent space and thus self-pressurizes the reagent to approximately the same hydraulic pressure as the hydraulic pressure on the carrier side of the membrane. The membrane can be protected from damage by placing a perforate housing member around the membrane.

The apparatus of the invention can further comprise means for flowing the carrier to a means for adding the sample to the carrier, means for flowing the carrier from the means for adding the sample to the carrier to one end of the channel, and means for flowing the carrier from the other end of the channel to a detector for detecting directly or indirectly the one or more components of the sample.

The invention is also an analytical chemistry method for effectively adding reagent to a flowing stream of liquid carrier in order to quantitatively analyze one or more components of a preselected volume of sample added into the carrier comprising: flowing the carrier and sample through a channel exposed to one side of a porous membrane having an average pore diameter of from greater than about 125 Å to about 5,000 Å and wherein the carrier contacts the membrane; contacting the other side of the membrane with the reagent; permeating the reagent across the membrane into the carrier; and flowing the carrier through a detector for detecting directly or indirectly said one or more components of the sample, wherein the pressure drop of the carrier from one end of the channel to the other end of the channel is low enough, e.g., less than 10 psig, to effectively prevent excessive leakage of the carrier across the membrane into the reagent.

The method of the invention can use a tubular or a sheet membrane and the membrane can comprise a polyolefin such a polypropylene.

The method of the invention can further include the step of pressurizing the reagent to a preselected pressure and wherein the pressure drop along the channel and the preselected pressure are low enouh to effectively prevent excessive permeation of the reagent into the carrier.

The method of the invention can also further include the step of sealing a space which is essentially completely filled with the reagent to thereby effectively self-pressurize the reagent in the space and wherein the pressure drop along the channel is low enough to effectively prevent excessive permeation of the reagent into the carrier.

Further advantages of the invention will in part be pointed out, and in part be apparent from the following detailed description when taken together with the accompanying drawings.

DETAILED DESCRIPTION OF THE INVENTION

Figure 1:
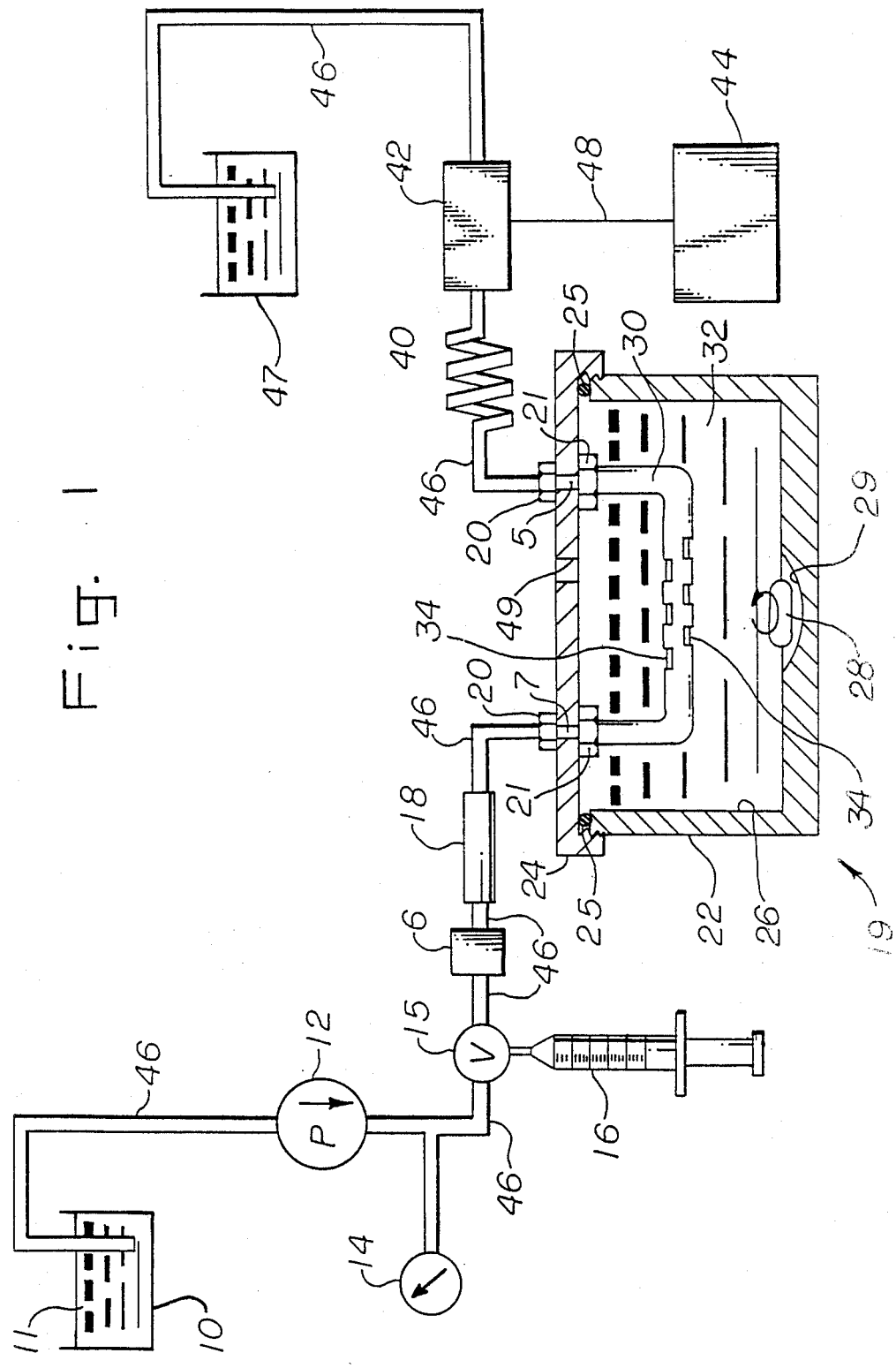
FIG. 1 is a schematic view of an apparatus for performing liquid chromatography using a tubular membrane reagent addition device in accordance with the principles and teachings of the present invention.

FIG. 1 illustrates a schematic view of a liquid chromatographic apparatus which is desirably used in practicing the invention, and which comprises a chromatographic column means 18. The chromatographic column means 18 comprises a housing and separating means typically in the form of a particulate packing or gel through which sample is eluted to separate the sample into component species. A variety of separating means may be used to construct a suitable chromatographic column, as described extensively, e.g., by Snyder et al., *Introduction to Modern Liquid Chromatography*, 2d Ed., 1979, pp. 740-746, and incorporated herein by reference.

A stream of eluent is formed from an eluent reservoir 10 containing eluent 11 to chromatographic column means 18. Eluent 11 is passed from eluent reservoir 10 to liquid chromatographic means 18 through a sample addition means such as sample injection valve 15 using a suitable liquid chromatographic pump 12 and conventional tubing 46. Pump 12 is equipped with an optional pulse damping/pressure measuring means 44.

Sample addition means, such as sample injection valve 15, is used to add sample into the stream of eluent, e.g., using a syringe 16. Sample and eluent are then passed to chromatographic column means 18. Sample and eluent can be passed through an optional guard column 6 prior to chromatographic column 18. Sample is chromatographically displaced in the column means 18 and component species thereof ultimately appear in the chromatographic column effluent. Chromatographic column effluent is delivered by way of additional conventional tubing 46 to a membrane reagent addition device generally indicated as 19.

The membrane reagent addition device 19 consists of a two-part device, a body 22 and a lid 24. The body 22 and lid 24 form a space 26 for holding reagent 32. Lid 24 is preferably threadably engagable with the body 22 and has an inlet port 7 and an outlet port 5. An O-Ring 25 is optionally disposed between the lid 24 and the body 22.

Lid 24, at inlet port 7, has connecting means 20 for connecting conventional tubing 46 to the liquid chromatographic column means 18. Connecting means 20 can be, for instance, a nut and ferrule combination. Preferably, connecting means 20 is made from stainless steel or a similarly inert material. Lid 24, at inlet port 7, also includes connecting means 21, connecting inlet port 7 to a first end of a tubular membrane 34 optionally covered with a centrally slotted tube 30. Tubular membrane 34 is connected at a second end with a second connecting means 21 for securing the second end of the membrane 34 to outlet port 5. Connecting means 21 is preferably a tube nut and ferrule. Outlet port 5 is fluidly connected with conventional tubing 46 and a second connecting means 20 to a detector 42.

Carrier fluid from the membrane reagent addition device 19 can then be passed to an optional mixing coil 40 which is disposed between outlet port 5 and detector 42. The optional means 40 or a functional equivalent is used to provide added reaction time for the sample species to be derivatized. If the optional means 40 is used, it is preferably maintained at a controlled temperature by suitable conventional temperature control means. In fluid communication with the optional means 40 is a detector 42 with means for detecting the component species of the effluent. Preferably, detector 42 is electrically connected by means 48 to a recorder 44 capable of displaying the results from detector 42 after detection. Detector 42 detects the desired property of the effluent such as light absorbance, fluorescence, or a similar property. Fluid from detector 42 is then passed to a waste reservoir 47 for disposal.

Data from detector 42 can be conveyed to a recorder 44 over means 48. Recorder 44 can be of any type suitable for recording the results from detector 42, such as a strip chart recorder, computer, visual display unit or similar device.

Referring also to FIG. 1, there is shown a preferred form of the membrane reagent addition device 19. The membrane reagent addition device 19 preferably includes a depression 29 disposed in the lower portion of the body 22. A stirring bar 28 is disposed within the depression 29 to facilitate adequate mixing of reagent while in the space 26, when body 22 is placed on a magnetic stirrer during permeation transfer.

Yet, in another embodiment of the invention, lid 22 can contain an additional port 49 through which the reagent 32 contained within the body 22 can be pressurized from apparatus external to the membrane reagent addition device 19 or the port 49 can be sealed shut in order to self-pressurize the reagent 32.

Figure 2:
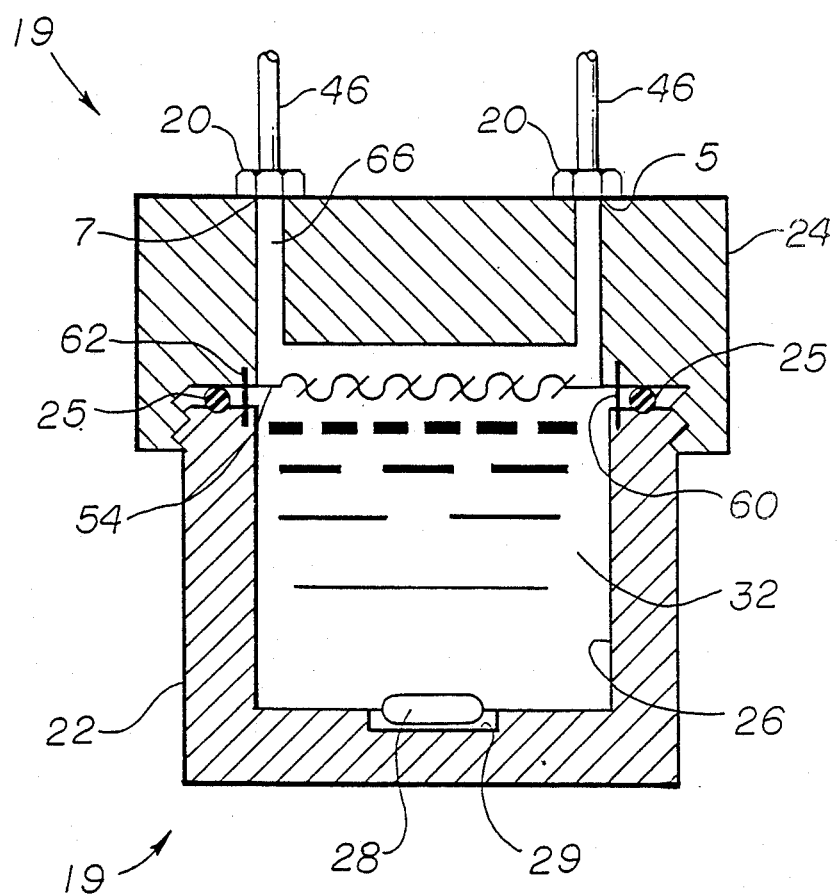
FIG. 2 is a cross-sectional view of a sheet membrane reagent addition device constructed in accordance with the principles and teachings of the present invention.

FIG. 2 shows yet another embodiment of a membrane reagent addition device 19 having a channel 66 formed in the lid 24 between inlet and outlet ports 5 and 7 for passing carrier from the chromatographic column 18 to the detector 42. At a central portion of the channel 66, the channel is open to the space 26 in the body 22. A flat membrane 54 is disposed over this opening completely covering the opening between the channel 66 and the chamber 26. The flat membrane 54 is positioned to cover the opening in the lid 24 and is secured by, for example, pins 60 and 62.

The invention is still further illustrated by reference to the specific teaching examples and comparative examples below.

Example 1

The membrane of the membrane reagent addition device generally described in FIG. 1 is protected from physical damage by preparing a short length, about 4 inches, of 0.04 inch I.D. and 1/16 inch O.D. 316 stainless steel tubing and repeatedly partially cutting through the 1½ inch center portion of the tubing with an abrasive wheel cutter leaving 1¼ inches, uncut at each end. About 22 cuts are made in the center 1½ inches of the tube. A 6 inch length of Celanese Celgard ® MHFX20 6008 (400 μM I.D.) tubular membrane is placed inside the stainless steel tube and sealed to the tube at each end using sealant, such as Weldwood brand waterproof wood glue or Dow Corning RTV ®. Silicone Rubber bathtub caulk injected between the membrane and the ends of the stainless steel tube. Once the sealer hardens, the ends of the membrane are cut flush with the ends of the protective stainless steel tube. The now completed membrane assembly is mounted in the membrane reagent addition device by detachably securing one end of the armored membrane to the inlet port, using a ferrule and nut and the other end of the armored membrane to the outlet port, also using a ferrule and nut.

EXAMPLE 2

The separation of various nitrophenols in waste water using a silica based reverse phase column, requires a carrier of a pH of less than 7 to 8. At a pH greater than this, the column degrades rapidly due to silica dissolution. However, detection is improved when the pH of the carrier is greater than 8. This example illustrates a separation at a pH of 6.1 and then, prior to detection, the conversion of the carrier pH to 9.2 for optimum detection using a self-pressurized reagent addition device.

In general, the analytical system is described in FIG. 1. The pump is an Altex Model 110. The analytical column is a Merck 10 micron RP-18, 4 mm I.D., 25 cm in length. A Rheodyne Model 7010 sample injection valve is used and fitted with a 100 μl loop. The detector is a Kratos Spectraflow Model 773 set for detection at 410 nm. The integrator—recorder is a Hewlett Packard Model 3380-A. The carrier is 60 percent acetonitrile—40 percent water, containing 0.02 M ammonium acetate, 0.005 M tetrabutylammonium hydroxide adjusted to a pH of 6.1 with a small amount of glacial acetic acid. The carrier flow rate is 1 ml per minute. The carrier pressure at the injection valve is 1,200 psig and at the membrane device the carrier pressure is about 50 psig. The delay means 40 between the reagent addition device and the detector is a 4.6×100 mm column filled with 140/200 mesh (105/74 micron) stainless steel granules. The reagent is concentrated ammonium hydroxide (29 percent strength). The membrane is sealed in a centrally slotted 1 mm I.D., 1.6 mm O.D., stainless steel tube as shown in FIG. 1 and discussed in detail in Example 1. The exposed length of the membrane is 40 mm. The membrane is Celanese Celgard porous polypropylene 0.4 mm I.D., 0.45 mm O.D., designated by the product code X-20 having eliptical pores of a width of about 200 Å and a length of about 2,000 Å. The reagent space of the membrane reagent addition device is completely filled with the reagent and then the reservoir is hermetically sealed.

When the carrier pump is turned on, the reagent pressure slowly rises to about 50 psig over a time span of about one-half hour and then stabilizes at 50 psig. The carrier emerging from the detector slowly changes pH from 6.1 to 9.2 pH over the first one-half hour of operation and then remains at a pH of 9.2. At this time, an injection of sample is made, and the chromatogram reproduced in FIG. 4 results. The sample is composed of 2.2 ppm dinitro-ortho-secondarybutyl phenol (DN), 2.3 ppm 2-hydroxy-3-secondarybutyl-5-nitrobenzene-1-sulfonate (2-OH) and 2.7 ppm 4-hydroxy-3-nitro-secondarybutylbenzene- -1-sulfonate (4-OH) in water.

Figure 3:
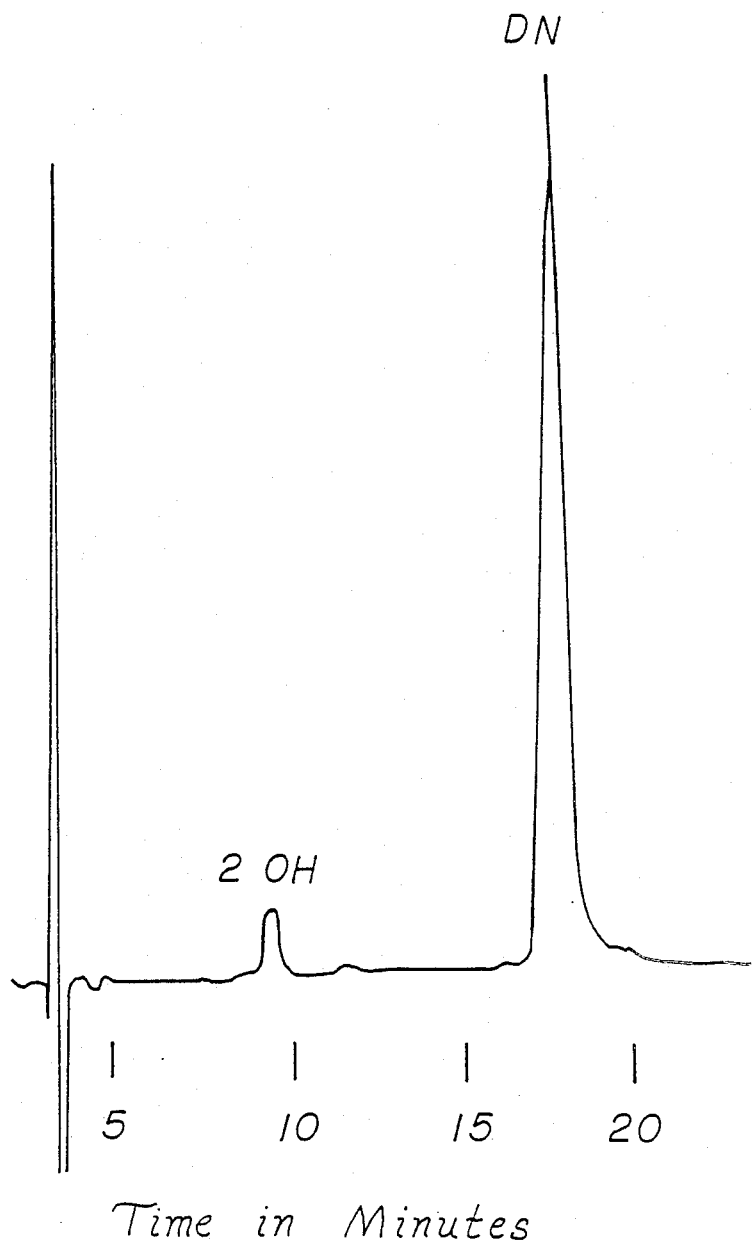
FIG. 3 is a chromatogram obtained without using the reagent addition device of the present invention for the liquid chromatographic analysis of selected nitrophenols.

For comparison, the chromatogram reproduced in FIG. 3 results when column effluent carrier is directly sent to the delay column without flowing through the reagent addition device 19 containing the membrane. In this configuration, the carrier emerging from the detector has a pH of about 6.1.

When the membrane device is not used in the system (see FIG. 3) the sensitivity of determination for 2-OH and especially 4-OH is low. In fact, no 4-OH peak is evident in the chromatogram. When the membrane device is used (see FIG. 4), sufficient ammonium hydroxide is added to the carrier stream to raise the pH to 9.2, resulting in an improved sensitivity 2-OH detection and especially 4-OH detection.

Since 34 microliters of reagent is needed to raise the pH of one milliliter carrier from 6.1 pH to 9.2 pH it is estimated that the reagent permeation rate into the carrier using the membrane device is 34 microliters per minute despite the relatively short length of tubular membrane used.

Figure 4:
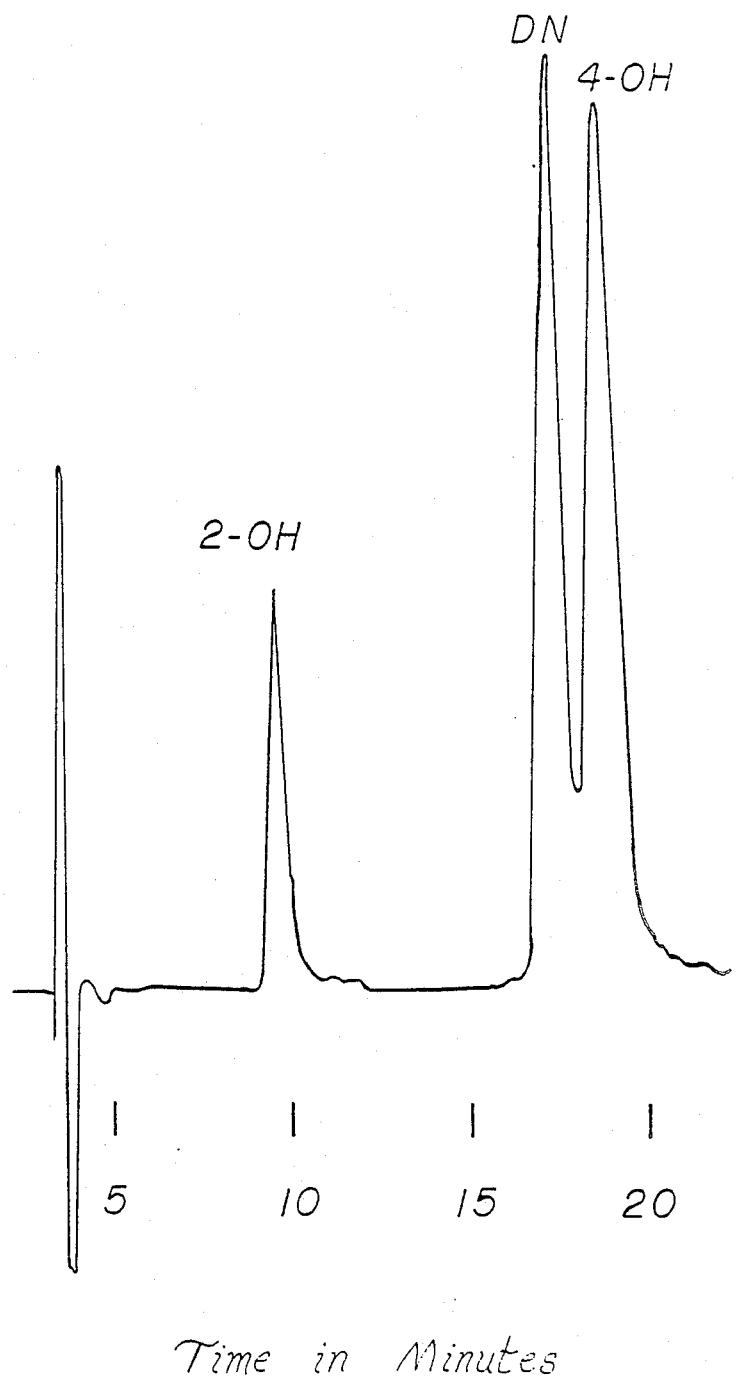
FIG. 4 is a chromatogram obtained with the use of the apparatus of the present invention for the liquid chromatographic analysis of selected nitrophenols.

The device of the present invention contributed no detectable additional bandspreading to the chromatographic peaks. The DN and 2-OH peaks in FIG. 3 or 4 are only about 1,450 $\mu$l wide which is a decrease in bandspreading caused by previous devices of about 450 $\mu$l.

EXAMPLE 3

The ortho-phthaldehyde/2-mercaptoethanol reaction is a particularly important reagent addition reaction in liquid chromatography, e.g., in the enhanced detection of primary amines. This example illustrates this reagent as used with the invention.

The system of Example 2 is used with the following changes: the carrier is 75 percent water, 25 percent acetonitrile, containing 1 gram of sodium acetate per liter of carrier. The column is a Du Pont Zorbax® ODS, 4.6 mm I.D. by 25 cm length. The reagent is composed of 1000 ppm each of ortho-phthaldehyde and 2-mercaptoethanol in 250 ml of water containing 6.6 g of boric acid. The reagent solution is adjusted to a pH of 10.3 with 10 percent sodium hydroxide solution. The detector is an LDC Fluorometer Model II. The size of the sample injection valve loop is reduced to a 20 $\mu$l volume. The reagent space of the membrane reagent addition device is completely filled with the reagent and then the reservoir is hermetically sealed.

Ortho-phthaldehyde reacts with primary amines in the presence of 2-mercaptoethanol to produce derivatives that are fluorescent at about 455 nm when excited at about 370 nm. Analysis of the effluent carrier from the device indicated that the rate of reagent permeation into carrier is about 7.5 $\mu$l per minute. The injected samples contain 1,000 ppm each of N-butylamine, glycine, L-leucine or L-tryptophan.

Chromatographic peaks are observed for each sample injection. However, when the carrier goes directly to the delay column, without flowing through the membrane device, no chromatographic peaks are observed upon injection of the samples above.

EXAMPLE 4

Peroxides and other relatively strong oxidizing agents will oxidize $I^-$ to $I_2$ to form highly colored $I_3^-$ in the presence of excess $I^-$. The reaction is useful, e.g., to determine the presence of peroxides or other strong oxidants in industrial process streams and products.

The system of Example 3 is used for the determination of peroxides with the following changes: the carrier is 50 percent isopropanol, 50 percent water. The detector is a Kratos Spectroflow 773 set for detection at 357 nm. The reagent is 10 percent tetrabutyl ammonium iodide in carrier. The reagent reservoir of the membrane reagent addition device is completely filled with reagent and then the reservoir is hermetically sealed. The samples injected are 200 ppb of peracetic acid or 35 ppm acetyl peroxide both dissolved in carrier. No analytical column is used. Instead, a 0.5 meter length of 0.76 mm I.D. by 1.6 mm O.D. conduit replaces the column to generate the approximately 1,000 $\mu$l of bandspreading that is expected if a column is used. As such then, this example demonstrates the utility of the present invention for the important analytical technique known as FIA.

Response peaks are observed for each injection of sample. However, when the carrier goes directly to the delay column, without passing through the membrane device, no response peaks are observed for the injection of the same samples.

Thus, this example demonstrates the utility of the present invention for the flow injection analysis of selected peroxides.

EXAMPLE 5

This example is the determination of a complex polyamine compound (Purifloc® C-31, a product of The Dow Chemical Company). Copper can complex with polyamine compounds and the complex can be determined at 275 nm.

The system of Example 4 is used with the following changes: the carrier is 80 percent water, 20 percent acetonitrile, containing 0.2 M NaCl, and adjusted to a pH of 4 using 1 M HCl. The injection loop is increased to a volume of 100 $\mu$l. The detector wavelength is changed to 275 nm. Reagent is 0.1 percent cupric chloride in carrier. The reagent reservoir of the membrane reagent addition device is completely filled with reagent and then the reservoir is sealed. The sample is 100 ppm Purifloc C-31 in carrier.

A response peak is observed for the injection of the sample. However, when the carrier goes directly to the delay column, without passing through the membrane device, no response peak is observed for the injection of the sample.

Copper can complex with polyamine compounds and the complex can be determined at 275 nm. The response peak observed with the use of the present invention indicates that this complexation occurred in this example and allowed the determination of the polyamine compound.

EXAMPLE 6

The system of Example 5 is used for the determination of hydroxyl containing compounds with the following changes: the carrier is 50 percent t-butyl alcohol, 50 percent water. The detector is changed to an electrochemical type known as the Chromatix CMX-20 using a nickel electrode. The reagent is 10 percnt tetraethylammonium hydroxide in carrier. The reagent reservoir of the membrane reagent addition device is completely filled with reagent and then the reservoir is hermetically sealed. The samples are 38 ppm formaldehyde in carrier, 100 ppm ethylene glycol in carrier, 10 ppm glucose in carrier and 25 ppm glycerol in carrier.

Many hydroxy containing compounds, but not t-butyl alcohol, react with Ni (III) at the electrode under basic pH conditions (pH from 10 to 12). The resulting Ni (II) is then converted back to Ni (III) by the detector and the current needed to do this is a function of the concentration of hydroxy compound injected.

A response peak is observed for the injection of each sample. However, when the carrier goes directly to the delay column, without passing through the membrane device, no response peak is observed for the injection of these same samples. The response peaks observed with the use of the present invention indicates that sufficient base is introduced into the carrier for the determination cited in this example.

Analysis of the carrier emerging from the detector indicated that about 12 µl per minute of reagent permeate into the carrier using the membrane device, resulting in a carrier pH of about 11.9.

EXAMPLE 7

The system of Example 6 is used for the determination of calcium and magnesium ions with the following changes: the carrier is 0.3 M sodium chloride (prepared using Baker Ultrex® grade NaCl which has a low concentration of impurity calcium and magnesium salts) in deionized water. The carrier flow rate is 1.1 ml per minute. The detector is the Kratos Spectraflow 773 set for 565 nm. The reagent is 0.023 M ortho-cresolphthalene complexone sodium salt (OCPC) in saturated sodium borate in deionized water. The reagent reservoir of the membrane reagent addition device is completely filled with reagent and then the reservoir is hermetically sealed. The delay column is removed and the membrane device is connected directly to the detector by means of 60 cm of 0.76 mm I.D.×1.6 mm O.D. conduit. The samples contain calcium or magnesium ions at the concentration of 10 ppm, 5 ppm, 2.5 ppm or 1.25 ppm in carrier.

Many divalent metal ions (including calcium and magnesium ions) chelate with OCPC to form strongly absorbing complexes. However, OCPC itself has a lower absorbance at 565 nm.

Response peaks are observed for the injection of each sample. However, when the carrier goes directly to the detector, without passing through the membrane device, no response peaks are observed for the injection of these same samples. The response peaks observed with the use of the present invention indicate that sufficient OCPC is introduced into the carrier by the present invention for the determinations cited in this example.

Figure 5:
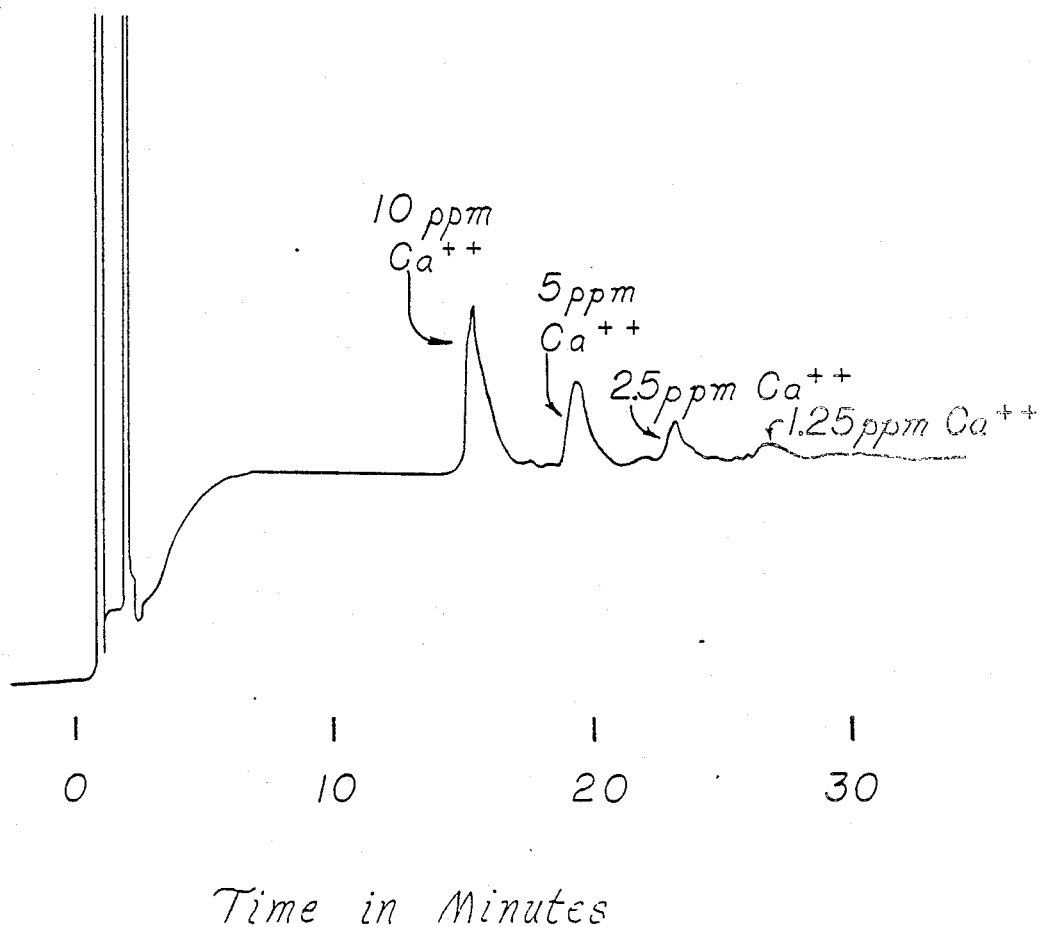
FIG. 5 is a chromatogram obtained by using the reagent addition device of the present invention for flow injection analysis of a series of sample injections containing calcium ions.

FIG. 5 shows an example of system performance from a start-up at zero minutes for a series of injections of calcium ions. The data in FIG. 5 indicates that the system is approximately at equilibrium and ready for use about 10 minutes after start-up.

The system is used intermittently over a 12 day period for 64 hours, i e., 8 hours a day for 8 days over about 2 weeks with 2 intervening weekends, without replacing the reagent solution. Table I shows data from this study.

TABLE I

| Data Over 12 Days Time With 64 Hours of Actual Use | | |
|---|---|---|
| | First Day AU | Last Day AU |
| Background Absorbance of Carrier at 565 Nanometers in Absorbance Units (AU) | 0.20 | 0.14 |
| Peak Height For a 100 Microliter Injection of a 10 ppm Calcium Ion Sample in Absorbance Units | 0.24 | 0.16 |

The data in Table I indicate an overall decrease in sensitivity and background absorbance of about 30 percent for the time period studied. However, during each days use, results were stable ±2 percent to ±5 percent relative, with no apparent pattern of drift. Since it is often common practice to recalibrate an analytical system at least every day, the long term drift of the system is acceptable for most applications. If it can be assumed that the decrease in background absorbance and responsiveness is due to reagent dilution in use, the system permeated OCPC reagent at a rate of about 10 µl per minute.

This example demonstrates the long term reliability of the present invention.

EXAMPLE 8

The separation and detection of various nitrophenols using a silica based ion-exchange column requires reagent addition for acceptable component detection in certain waste waters.

The experiment is conducted using a nonsealed and nonpressurized (atmospheric pressure) reagent addition device and the following solutions and apparatus. The carrier is 35 volume percent methanol and 65 volume percent water. This carrier also contains 0.08 M sodium perchlorate and 0.04 M ammonium acetate. The pH of the carrier is finally adjusted to 6.0 by adding acetic acid. The carrier pump is an Altex Model 110A set for a flow rate of 1.0 ml per minute. The injection valve is a Rheodyne Model 7120 with a 20 µl injection loop. The analytical column used is a Whatman Partisil SAX 10/25 (4.6 mm×250 mm). The effluent carrier from the analytical column is conducted to the inlet port of the membrane reagent addition device. The outlet port of the device is connected to a Laboratory Data Control Model 1203 detector set for a detection wavelength of 410 nm. The detector signal is sent to a Hewlett Packard Model 3380A recorder/integrator.

The reagent is about 30 weight percent ammonium hydroxide. The sample contains a mixture of 2.2 ppm dinitro-ortho-secondarybutyl phenol (DN), 2.3 ppm 2-hydroxy-3-secondarybutyl-5 nitrobenzene-1-sulfonate (2-OH) and 2.7 ppm 4-hydroxy-3-nitro-secondarybutyl-benzene-1-sulfonate (4-OH) in water.

Figure 6:
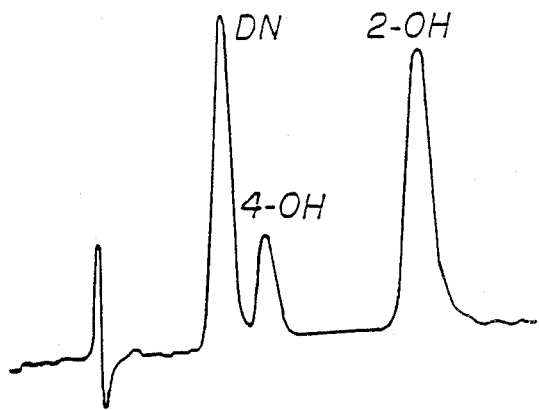
FIG. 6 is chromatogram of selected nitrophenols obtained by using the apparatus of the present invention employing a reagent of 30 weight percent ammonium hydroxide.
Figure 7:
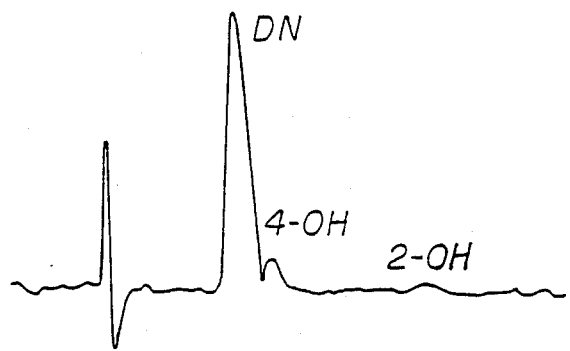
FIG. 7 is a chromatogram obtained by using the apparatus of the invention as in FIG. 6 but replacing the reagent in the membrane reagent addition device with carrier.

When a sample injection is made, the chromatogram shown in FIG. 6 results. When the reagent in the membrane reagent addition device is replaced with carrier, the chromatogram shown in FIG. 7 results. The use of a reagent of 30 weight percent ammonium hydroxide results in a pH shift of the carrier from 6 to 9. At a pH of about 9, both the 4-OH and 2-OH components showed beneficially high detectability as is shown when comparing FIG. 6 and FIG. 7.

EXAMPLE 9

Figure 8:
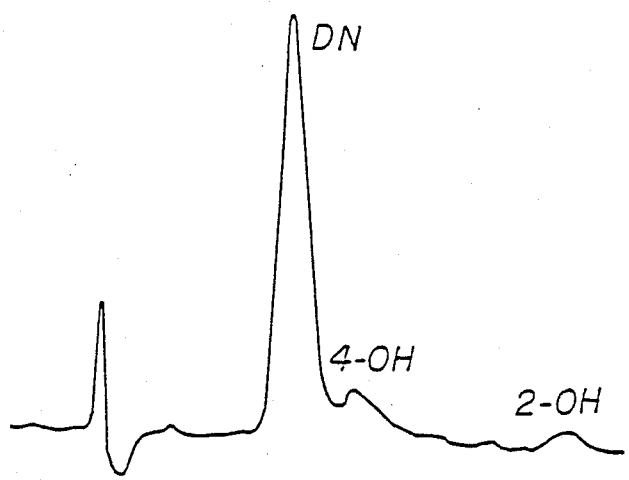
FIG. 8 is a chromatogram obtained by using the apparatus of the present invention as in FIG. 6, and wherein a mixer-delay means is additionally disposed between the membrane reagent addition device and the detector.

Added to the system of Example 8 is a coil of 0.25 mm I.D.×1.6 mm O.D. Teflon conduit. The coil is disposed between the reagent addition device and the detector with a length sufficient to give a back pressure inside the tubular membrane of about 15 psig. The reagent used in this device is about 30 weight percent ammonium hydroxide. When a sample is injected, the chromatogram shown in FIG. 8 results. The carrier back pressure in the porous hollow fiber membrane prevents sufficient reagent from permeating into the carrier stream to change the carrier pH significantly.

Figure 9:
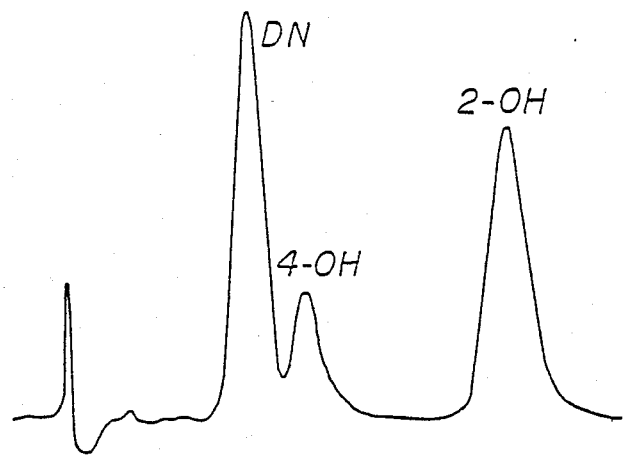
FIG. 9 is a chromatogram obtained by using the apparatus of the present invention as in FIG. 8 wherein the mobile reagent within the membrane reagent addition device is externally pressurized.

A compressed air line is attached to the port 49 of the reagent addition device and the reagen chamber is pressurized to about 16 psig. When a sample is injected, the chromatogram shown in FIG. 9 results. Pressurizing the reagent chamber to a pressure nearly the same as the carrier pressure within the tubular membrane results in sufficient reagent permeation to alter the carrier pH to about 9 and thereby significantly increase the absorbance of the 4-OH and the 2-OH compounds as is shown when comparing FIG. 8 with FIG. 9.

What is claimed is:

1. In a method of reagent addition to an effluent stream in liquid chromatography wherein the stream is under pressure, comprising the steps of contacting the effluent stream with one side of a two sided liquid and reagent permeable membrane, contacting the other side of the membrane with a liquid mobile reagent contained in a chamber, wherein the improvement comprises the step of: pressurizing the mobile reagent by essentially completely filling the chamber with the mobile reagent and hermetically sealing the chamber, so that permeatiion of effluent across the membrane into the mobile reagent pressurizes the mobile reagent and so that the mobile reagent can be permeated into the effluent stream.

2. The method of claim 1 wherein the membrane is tubular in shape.

3. The method of claim 1 wherein the membrane is flat in shape.

4. The method of claim 1 wherein the membrane comprises a polyolefin material.

5. In a method of reagent addition to a carrier stream in flow injection analysis wherein the stream is under pressure, comprising the steps of contacting the carrier stream with one side of a two sided liquid and reagent permeable membrane, contacting the other side of the membrane with a liquid mobile reagent contained in a chamber, wherein the improvement comprises the step of: pressurizing the mobile reagent by essentially completely filling the chamber with the mobile reagent and hermetically sealing the chamber, so that permeation of carrier across the membrane into the mobile reagent pressurizes the mobile reagent and so that the mobile reagent can be permeated into the carrier stream.

6. The method of claim 5 wherein the membrane is tubular in shape.

7. The method of claim 5 wherein the membrane is flat in shape.

8. The method of claim 5 wherein the membrane comprises a polyolefin material.

* * * * *